United States Patent [19]

Thompson

[11] 4,402,946

[45] Sep. 6, 1983

[54] ANTITHROMBOTIC TREATMENT

[75] Inventor: Ralph B. Thompson, Oak Brook, Ill.

[73] Assignee: T & R Chemicals, Inc., Clint, Tex.

[21] Appl. No.: 337,175

[22] Filed: Jan. 5, 1982

Related U.S. Application Data

[63] Continuation-in-part of Ser. No. 271,851, Jun. 16, 1981, abandoned, which is a continuation-in-part of Ser. No. 218,413, Dec. 22, 1980, abandoned.

[51] Int. Cl.³ .................. A61K 31/70; A61K 31/715; A61K 31/095; A61K 31/115
[52] U.S. Cl. ..................................... 424/180; 424/325; 424/331; 424/333; 424/334; 424/335
[58] Field of Search ............... 424/162, 180, 315, 325, 424/324, 331, 333, 334, 335

[56] References Cited

U.S. PATENT DOCUMENTS

| | | | |
|---|---|---|---|
| 2,367,302 | 1/1945 | Moore | 424/331 |
| 3,836,639 | 9/1974 | Teler | 424/101 |
| 3,906,109 | 9/1975 | Roehm | 424/325 |

OTHER PUBLICATIONS

Chao, Thrombos. Haemostas (Stuttg), vol. 35, 1976, pp. 717-736.
Shulman, Chem. Abs., vol. 47, 1953, p. 9386.
Gunnison, Fd. Cosmet. Toxicol, vol. 19, 1981, pp. 667-682.
Elias, Abstract of Thromb. Diath. Haemorrh, vol. 18 (3-4) 1967, pp. 499-509.
Torda, Abs. of Anaesth, Intens. Care, 1, 293, (1973).
Bourbon, Abs. of J. Eur. Toxicol. vol. 4, No. 3, pp. 205-207 (1971).
Chem. Abs. 9th Coll. Index, p. 37336CS & vol. 82, Ab. No. 107247f (1975).
Kikugawa, J. Pharm. Sci., vol. 61, 1972, pp. 1904-1907.
Rost, "Comparative Invst. of the Pharmacol. Effects of Organically Bonded Sulfurous Acids and of Neutral Sodium Sulfite" in Arb. A.D. Kaiserlichen Gesundheitsamte, vol. 21, 1904, p. 312.

Primary Examiner—Anna P. Fagelson
Attorney, Agent, or Firm—Cushman, Darby & Cushman

[57] ABSTRACT

Certain salts of carbonyl sulfur dioxide adducts are found to demonstrate anticoagulant and/or venous antithrombotic activity.

20 Claims, No Drawings

ANTITHROMBOTIC TREATMENT

CROSS-REFERENCE TO RELATED APPLICATIONS

This application is a continuation in part of my earlier filed U.S. patent application U.S. Ser. No. 271,851 filed June 16, 1981, now abandoned, which in turn is a continuation in part of my earlier filed U.S. application U.S. Ser. No. 218,413 filed Dec. 22, 1980, which is now abandoned. The disclosure and contents of all such prior parent applications are incorporated herein by reference.

BACKGROUND OF THE INVENTION

Inorganic salts of sulfurous acid have heretofore been discovered by Jose Antonio Arias Alvarez to have anti-coagulant and antithrombotic properties, see U.S. Ser. No. 227,382 filed Jan. 22, 1981, now abandoned in favor of continuation-in-part application Ser. No. 271,850 filed June 6, 1981, now abandoneed in favor of copending application Ser. No. 337,176 filed Jan. 5, 1982.

Various carbonyl bisulfite adducts have heretofore been used for commercial purposes, such as control of mold in seeds. Glyoxal bisulfites have been used medically to inhibit blood platelet aggregation; glyoxals are 1,2-dicarbonyl compounds and the bisulfite adduct is used only as a carrier for the glyoxal. So far as is known these carbonyl bisulfite adducts have never heretofore been known to have anticoagulant or antithrombotic properties.

Anticoagulants and antithrombotics are a group of compounds with diversified pharmacologic actions, used in a variety of chemical thrombotic disorders. Thrombotic disorders are generally divided into venous thrombosis and arterial occlusive disorders. Venous thrombosis of the lower extremities is important because it can cause pulmonary embolism which may be fatal. Heparin and warfarin are commonly used in clinical medicine for prevention and treatment of deep venous thrombosis and pulmonary embolism. Their pharmacological actions are in the inhibition of blood coagulation activity (i.e., heparin) or of synthesis of coagulation factors (i.e., warfarin). Platelets play an important part in arterial thrombosis. Drugs that inhibit platelet aggregation are generally regarded as being potentially usefull for prophylactic therapy of arterial thrombotic disorders, including, for example, stroke, myorcardial infarction and peripheral vascular disease. Despite the availability of many agents which possess anti-platelet aggregating properties, only a few are currently under clinical trials (for example, aspirin, dipyridamole, sulfinpyrazone). None of these agents exhibit unequivocal efficacy. Compounds with more specific pharmacological action are urgently sought in order to provide better medical care for patients with these serious disorders.

An anti-platelet aggregatory agent is a substance which inhibits platelet aggregation.

An antithrombotic agent is a substance which inhibits formation or development of a thrombus (or thrombosis). For present patent purposes, it will be understood that the term "thrombus" or equivalent includes the subject matter of the term "embolus" unless otherwise specifically indicated. In general, an antithrombotic agent may display, in the presence of mammalian blood or appropriately prepared plasma, anticoagulant activity and/or anti-platelet aggregatory activity.

BRIEF SUMMARY OF THE INVENTION

There has now been discovered a class of agents, the members of which when introduced into blood, as by ingestion, injection, absorption, or otherwise introduced into a mammal (including man), produce anticoagulant effects and antithrombotic effects (especially venously) in mammals (including man) when used in an antithrombotically effective amount, all as taught herein.

The active agents of the present invention are salts of carbonyl sulfur dioxide adducts which display anticoagulant and antithrombotic activity. Presently preferred agents are representable by the formula:

where:
R is a radical selected from the group consisting of hydrogen and hydroxymethyl,
$R^1$ is radical selected from the group consisting of hydrogen straight chain alkyl radicals each containing a total 2, 3, 4, or 5 hydroxylated carbon atoms, and a residue from a polysaccharide capable of reducing Fehling's solution,
X is selected from the group consisting of alkali metals and ammonium.

One presently preferred compound of formula (1) is sodium formaldehyde bisulfite. Sodium is presently preferred as X.

Antithrombotic agents of this invention are used in venous thrombosis.

Examples of clinical thrombotic conditions include stroke (as a cerebral vascular thrombosis), myocardial infarction (coronary artery disease), peripheral vascular disease, cardiac valve replacement, deep vein thrombosis, pulmonary embolism, and the like.

The mechanisms by which the active agents function is presently unknown; however, a prolongation of normal blood coagulation time appears to be associated with use thereof in the manner taught by the present invention.

In one aspect, the present invention is directed to a method for control of, and/or prevention of, an embolus or a thrombus in man by oral ingestion and/or injection of a pharmaceutically effective amount of sodium formaldehyde bisulfite and/or other compound(s) within the scope of active agents of this invention.

In another aspect, the present invention provides symptomatic and objective improvement in a thrombotic (including cardiovascular) disease condition, such as, for example, an abnormal coagulation, or an intravascular thrombosis, in man. By the term "symptomatic improvement", as used herein, reference is had to an improvement in a patient's subjective symptoms (e.g., as reported by the patient). By the term "objective improvement", as used herein, reference is had to a measurable and objective change in a patient's condition.

Naturally, an active antithrombotic agent of this invention is used, if at all in a mammal, at a pharmaceutically effective dose rate—that is, at a dose rate which is below the level of toxicity or of production of undesired side effects. Because of biological complexities, the complete biological effects of the active agents of this invention are not now known.

Other and further aspects, objects, purposes advantages, aims, utilities, features and the like will be apparent to those skilled in the art from a reading of the present specification.

DETAILED DESCRIPTION

More particularly, this invention concerns a process for treating a human or other mammal wherein there is introduced orally and/or by injection into such mammal a pharmaceutically effective amount of active agent as an antithrombotic.

Sulfite and/or bisulfite anions do not normally occur in human tissues or blood, so far as is now known.

In medicine, for example, arterial thrombosis is diagnosable by clinical manifestations, by arteriography, and recently, by an Indium[111] platelet labeling technique (see, for example, the article entitled "Differential Effects of Two Doses of Aspirin on Platelet-Vessel Wall Interaction In Vivo" by K.K. Wu et al being published in the Journal of Clinical Investigation, August 1981.

Also, in medicine, for example, it is detectable from patient conditions symptomatically perceivable by a skilled medical practioner and well known to the art of medicine. Objectively, several methods including venography, impedance plethysmography, doppler ultrasound, and the I[125]-fibrinogen test; see, for example, the article Kakka, Archives of Surgery, Vol., 104, pg. 152 (1972) and Kelton, J. G. et al, Journal of Clinical Investigation, Vol. 62, pgs. 892–895 (1978).

The present invention does not contemplate feeding a normal patient (that is, one not suffering from a thrombotic condition) an active agent of this invention at a pharmaceutically effective dosage as indicated herein.

By the term "thrombotic condition" as used herein, reference is had both to:

(a) an existing thrombus (including an embolus); and/or (b) an incipient thrombus (including an incipient embolus.

An "incipient thrombus" or "incipient thrombotic condition", as such a term is used herein, can exist in a patient who has a predisposed condition for development of a thrombotic condition. For example, in a diabetes mellitus, hyperlipedemia, and the like are conditions which predispose a patient to arterial thrombosis.

Those skilled in the practice of medicine routinely determine the presence of a thrombotic condition (including an actual thrombus) in a patient. Such a condition is determined for the present invention preferably by state of the art techniques. Such determination techniques are known to the prior art and do not as such constitute a part of the present invention.

Preferably, to practice this invention in vivo, one introduces at least one active agent of this invention into the blood of a patient, such as a human, the equivalent of from about 1 to 100 milligrams per kilogram of mammal body weight (including human) per day, although larger and smaller dose rates may be employed, if desired, within the spirit and scope of this invention. The exact amount or dose in any given case is selected so as to be sufficient and appropriate for achieving a desired antithrombotic effect. Injection is accomplished with an active agent in solution.

In general, to initiate practice of the present invention, such an introduction may be commenced at a dosage rate with the range above indicated as soon as a thrombotic condition (or a thrombus) is found to exist in a patient.

Thus, and for example, in a preferred practice of this invention, as a first step, a determination is made that a patient suffers from a thrombotic condition. Then, one starts orally feeding and/or injecting such patient with at least one active agent of the present invention at an effective dose rate in the range above indicated. Presently, a more preferred dose rate is believed to be from about 2 to 50 mg/kg per day. Preferably, at least two or three spaced doses per day are employable, each such dose being conveniently administered around meal time. Any convenient dose arrangement can be employed.

Not uncommonly, it is desirable or necessary to start treatment immediately upon the discovery of a patient's thrombotic condition to avoid damage, injury, or perhaps even death of the patient, as from an embolus. If oral administration is not convenient or rapid enough for a situation, the active agent can be directly introduced by injection into a patient, if desired, such as intraveneously, intraperitoneally, intramuscularly, subcutaneously, or the like. Absorption through a membrane, such as a dermal layer, may also be used, as when an active agent is dissolved in an appropriate solvent. Suppositories can be used to achieve absorption. When an active agent is so directly introduced, it is preferably dissolved in an aqueous medium wherein the total amount of active agent introduced into such medium is preferably within the range from about 1 to 11 weight percent (based on the total solution weight). Distilled water is a presently preferred solvent for such a medium. If desired, conventional, standardized aqueous media may be used as vehicles for such introduction; for example, standard saline solutions can be used as vehicles.

A present preference is to withdraw samples of blood from a patient undergoing treatment and to measure platelet aggregation. One method, described in the paper by Born, G., Nature 194, pp. 927–929 (1962), may be used for this purpose if desired.

After administration has started, the dose rate is preferably adjusted to a value which is sufficient to disrupt platelet function and/or coagulation factors and thereby achieve a desired antithrombotic effect.

An active agent of this invention, for example, is characteristically capable of exhibiting platelet aggregation both in vitro and in vivo. Also such an active agent is characteristically capable of lengthening both PT (prothrombin time) and PTT (blood partial thromboplastin time) in vitro. Dose rate of active agent is presently believed to be directly proportional to resulting effects upon blood factors, such as inhibition of platelet aggregation or the like. Consequently, under this preferred procedure, use of an active agent at a suitable dose for an individual patient ameliorates that patient's thrombotic condition.

Selected blood parameters of a patient are preferably determined before dosing with active agent is started, as when time permits. Preferably, a dose rate adjustment is accomplishable after administration of an active agent has commenced and is continuing. The amount of adjustment (or incremental change in dosage) is determinable by comparing a patient's measured values during administration of active agent to desired values (such as the patient's own starting corresponding values, normal species e.g. human, values, or the like). Inhibition of platelet aggregation can be used for measurements. Then, the deviation, if any, from the patient's such measured values is compared to such desired values (the patients starting values, normal species values, or the like). Then, a change in dose rate may be undertaken to correct for any deviation so determined.

For instance, in humans normal values for platelet aggregation are dependent upon the particular agent used for stimulation. For example, when adenosine diphosphate (ADP) at a 3 millimolar concentration is employed, platelet aggregation values fall typically in the range between 50% to 100% of light transmission. Other stimulation agents include collagen, epinephrine, arachidonic acid, and the like.

Also, for instance, in humans, normal PT values are believed to fall in the range from about 11 to 13 seconds while normal PTT values are believed to fall in the range from about 25 to 41 seconds. If PT values and/or PTT values could be measured in a given patent, as for purposes of achieving a desired antithrombotic effectiveness, it is currently estimated that a lengthening of PTT value of from about 1.5 to 2 times a PTT value in such normal range in a given starting patient is appropriate (suitable) for antithrombotic effectiveness, which is equal to a lengthened PTT value for a given patient of from about 45 to 60 seconds; such an estimate is consistent, for example, with the lengthened PTT values achieved in the human use of heparin, a prior art agent sometimes previously employed as an antithrombotic agent. Similarly, it is currently estimated that a lengthening of PT value of about two times a PT value in such normal range in a given starting patient is appropriate (suitable) for antithrombotic effectiveness, which is equal to a lengthened PT value for a given patient of from about 22 to 26 seconds; such an estimate is consistent, for example, with the lengthened PT values achieved in the human use of coumadin (warfarin), a prior art agent sometimes previously employed as an antithrombotic agent. The active agents of the present invention, contrary to such prior art agents, appear to affect in vitro both PT and PTT values in a given patient, surprisingly. The mechanism by which the present active agents work is apparently substantially different from, and not comparable to, the prior art agents. Study and evaluation of the active agents of this invention continues.

Contrary to such prior agents (like heparin and coumadin) the active agents of the present invention appear to affect both blood coagulation factors and platelet aggregation. Conveniently and preferably, measurements of blood factors are carried out periodically, such as every 3 to 7 days, on a patient undergoing treatment under the practice of this invention.

An active agent can be orally consumed in the form of a capsule, a tablet, or the like, or in the form of a solution (e.g. aqueous). Also, an active agent can be injected in the form of an aqueous solution.

A particularly presently preferred antithrombotic field of use is in post operative patient treatment, as when arteries or deep veins may be involved in, or threatened by, a thrombotic condition.

By way of explanation, as those familiar with mammalian anatomy appreciate, the venous system of the lower extremities consists of superficial and deep veins. Because of the manner in which the deep veins interconnect and supply blood to the heart and lungs, a thrombus occurring in the deep veins, but not in the superficial veins, can become the source of a blood clot which is moved through the veins and becomes lodged in the lungs, resulting in a pulmonary embolus, which can have obvious catastrophic effects (including causing death). Examples of deep veins include the iliac, the femoral and the topliteal. The prevention of pulmonary emboli following surgery affecting the deep veins in the lower extremities is a significant medical problem. One solution to this problem is to prevent thrombi from occurring and/or developing in deep veins. To achieve this solution, active agents of this invention appear to be well suited. Thus, in one such mode of this invention, one achieves symptomatic and objective improvements in a patient during postoperative care following surgery affecting deep veins by inhibiting intravascular thrombosis (including embolism).

At the present time, available data indicates that sodium formaldehyde bisulfite has a minimal effect on inhibition of platelet aggregation.

One presently preferred starting material for making a compound of formula (1) is formaldehyde.

Sodium formaldehyde bisulfite may be purchased commercially.

The term "monosaccharide" as used herein has reference to an organic compound which is an hydroxyaldehyde or an hydroxyketone which contains on hydroxyl group adjacent to a carbonyl group. The term "polysaccharide" as used herein has reference to a saccharide which contains moree than one monosaccharide in its structure. Polysaccharides and monosaccharides useful in this invention are each capable of reducing Fehling's solution. For present purposes, a one gram quantity of a saccharide is dissolved or dispersed in 25 grams of distilled water and 5 milliliters of Fehling's solution is added thereto. If there is a precipitate of cuprous oxide formed upon standing or upon warming to 50° C., then the saccharide is usable in the practice of this invention as a starting material.

A presently preferred class of starting materials comprises monosaccharides each having a carbonyl group, which are selected from the group consisting of aldoses and ketoses wherein each ketose has its carbonyl group in the 2-position. More preferred such monosaccharides each contain five or six carbon atoms per molecule. Presently preferred aldoses are selected from the group consisting of glucose, ribose, xylose, arabinose, galactose, and the like. A presently preferred ketose is fructose, or the like.

Another preferred class of starting materials comprises polysaccharides, such as a dextrin prepared by acid treatment of starch, maltose, cellobiose, lactose, melibiose, manninotriose, and the like.

One convenient preparation technique for preparing a saccharide/bisulfite compound of formula (1) above is to agitate a saturated aqueous solution of the desired bisulfite salt with at least a stoichiometric amount of a carbonyl compound which corresponds to the desired carbonyl sulfur dioxide adduct desired. In the case of monosaccharide adducts, one or more equivalents of the sugar is (are) mixed with one equivalent of the bisulfite compound in aqueous medium to provide a solution of the bisulfite adduct to the sugar. Solutions containing more than about 60 weight percent water are preferred. Other known synthetic methods may be used if desired in order to obtain the saccharide-bisulfite compounds as solids as for oral ingestion.

Aqueous solutions represent a practical way of practicing this invention. The agents of this invention do not oxidize readily in air-exposed aqueous solutions.

In one preferred mode of using this invention, an aqueous solution containing from about 1 to 10 percent by weight of an active agent of this invention, preferably sodium glucose bisulfite or sodium formaldehyde bisulfite, is used. Then, such solution is injected into, or orally consumed by, a patient at a total (or accumulated) dose rate preferably ranging from about 1.0 to 50 mg per each kg of body weight per day, more preferably in the form of at least two spaced doses per day, and still more preferably in the form of at least three spaced doses per day, such a dose being preferably taken around meal time. Solid or encapsulated active agents may be orally consumed alternatively.

One presently preferred composition for use in the practice of this invention is prepared by dissolving a desired quantity of an alkali metal bisulfite in an aqueous glucose solution, such as a standardized medical solution of about 5 weight percent glucose in distilled water (of the type used for intravenous adminstration to a patient).

The agent used in an aqueous solution can be directly used in accordance with the teachings of this invention, in which such a solution can be dispensed dropwise, or such a solution can be encapsulated, or the like, and used as measured dosage units, as desired. For example, an aqueous solution containing 5 weight percent of sodium glucose bisulfite or sodium formaldehyde bisulfite can be injected into a patient or it can be directly consumed by a patient as drops (e.g., from about 5 to 30 drops per meal for each of the two or three meals eaten by such patient per day, depending upon an individual patient's body weight, or the like).

Symptomatic improvement in varicose veins and in hemorrohoids is observable when using an active agent such as sodium glucose bisulfite.

EMBODIMENTS

The present invention is further illustrated by reference to the following examples. Those skilled in the art will appreciate that other and further embodiments are obvious and within the spirit and scope of this invention from the teachings of these present Examples taken with the accompanying specification.

Preparation of Active Agents

Example A

A solution of sodium formaldehyde bisulfite is prepared by dissolving commercially available solid sodium formaldehyde bisulfite in distilled water at room temperature to form a 3 percent by weight aqueous solution.

Example B

Another solution of sodium formaldehyde bisulfite is prepared by dissolving commercially available solid sodium formaldehyde bisulfite in distilled water at room temperature to form a 10 percent by weight aqueous solution.

Example C

A capsule of sodium formaldehyde bisulfite is prepared by charging to each of standard gelatin capsules sufficient sodium formaldehyde bisulfite to make 25 mg of active agent.

Example D

The procedure of Example C is repeated except that 50 mg capsules of active agent are prepared.

Example E

A solution to contain 2% by weight of sodium bisulfite is prepared by dissolving the desired amount of bisulfite with one equivalent of glucose.

Example F

The procedure of Example E is repeated except that four equivalents of glucose are used.

Example G

The procedure of Example F is repeated except that the product is heated on a steam bath (about 90° C.) for one hour.

Example H

The procedure of Example E is repeated except that in place of glucose, fructose is used.

Example I

The procedure of Example E is repeated except that in place of glucose arabinose is used.

Example 1

In vitro assays of the product of certain above Examples are conducted for coagulation factors as taught in a standard textbook, entitled: "Human Blood Coagulation, Haemostasis and Thrombosis", edited by Rosemary Biggs, published by Blackwell Scientific Publication, Oxford England (2nd Edition), pages 670–705, 1976. The results are shown in Table I below.

Example 2

Evaluation of the antithrombotic effect of sodium formaldehyde bisulfite was carried out on a rabbit as described in Kelton et al: "Thrombogenic Effect of High Dose Aspirin in Rabbits", Journal of Clinical Investigation, Volume 62, pages 892–895, (1978). When the rabbit was treated with 50 mg/kg of $CH_2SO_3Na$ (OH) (e.g., sodium formaldehyde bisulfite), the thrombus disappeared more rapidly than in a control animal.

Example 3

A rabbit is fed orally by gavage about 50 mg/kg in two spaced doses of sodium formaldehyde bisulfite as the solution of Example A. After a period of 1 day, the animal's blood is analyzed for PT and PTT values, and it is found that both these values have lengthened compared to corresponding values from the blood of an otherwise untreated control rabbit.

Example 4

Using the procedure of Example 1, PT and PTT values for sodium formaldehyde bisulfite are obtained as shown in Table II below:

TABLE II

|  | PT | PTT |
|---|---|---|
| Control | 12.5 | 33.4 |
| 0.01 Molar Sodium formaldehyde bisulfite | 24.4 | 54.6 |

EXAMPLE 5

Two jugular veins on a normal, healthy rabbit are exposed and one of the veins is systematically damaged by clamping in two longitudinally spaced places. The rabbit is then continuously infused with aqueous sodium formaldehyde bisulfite at the rate of 400 mg/hr/kg body weight (0.92 g/hr for animal body weight of 2.3 kg for 3 hours). The rabbit is then injected with fibrinogen labeled with $I^{125}$. After 5 hours, the damaged jugular vein is evaluated for radioactive count with a Geiger counter. When the amount of radioactivity on the rabbit infused with sodium formaldehyde bisulfite is compared to the count of the jugular vein of a rabbit infused with normal saline solution, the rabbit from the normal saline solution has more radioactivity than his counterpart infused with sodium formaldehyde bisulfite.

It is concluded that sodium formaldehyde bisulfite shows a definite positive effect of decreasing thrombus formation as in the jugular vein. This iodine 125 evaluation technique is described by Kakkar in Archives of Surgery, Vol. 104, pg. 152 (1972) and by Kelton, J. G. et al, Journal of Clinical Investigation, Vol. 62, pgs. 892–895, (1978). Closely similar results were achieved with a second rabbit. Other rabbits, similarly evaluated died, apparently because of overdose by the infusion technique.

Example 6

A rabbit is injected with about 72 mg/kg of body weight of sodium formaldehyde bisulfite. After a period of 5 hours, a blood sample was withdrawn and centrifuged at 1000 r.p.m. (220 g) for 10 minutes to give a platelet rich plasma. The material was evaluated for platelet aggregation by the method described in Wu et al (ref. cited above) and it was found that aggregation of platelets was markedly decreased in comparison with an untreated rabbit. It is concluded that sodium formaldehyde bisulfite is an agent which inhibits thrombus formation in vivo. Similar test results were achieved with other rabbits so tested. It is estimated that this material is 1000 times less effective than sodium bisulfite.

Example 7

Platelet rich plasma from rabbits and men was prepared by the centrifugation technique referenced in Example 6. Using ADP (adenosine diphosphate) or arachidonic acid as a stimulus, rapid aggregation of platelets occurred. When the so stimulated blood had been treated with sodium formaldehyde bisulfite, there was a strong inhibition of platelet aggregation. This procedure is described in the article by Born, Nature, Vol. 194, pgs. 927–929 (1962). The results demonstrate that sodium bisulfite causes inhibition of platelet aggregation in vitro.

Example 8

Bisulfite adducts were prepared from acetone, cyclohexane, benzaldehyde and 2-octanone. When evaluated by the Biggs' technique, they had a minimal effect on PT and PTT at 0.5 mg/ml.

Example 9

A normal monkey is fed, through food which is on his normal diet, sodium glucose bisulfite at a dose rate estimated to be about 5 mg. per kg. of body weight per day. A reduction in the animals starting blood pressure is observed within about a month.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth in the hereto-appended claims.

I claim:

1. A method for treating a thrombotic condition in a mammal comprising adminstering to such mammal an antithrombotically effective amount of at least one compound of the formula:

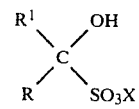

where:
R is a radical selected from the group consisting of hydrogen and hydroxymethyl,
$R^1$ is a radical selected from the group consisting of hydrogen and straight chain alkyl radicals each containing a total of 2, 3, 4, or 5 hydroxylated carbon atoms, and a residue from a polysaccharide capable of reducing Fehling's solution, and
X is selected from the group consisting of alkali metals and ammonium.

2. A method for treating a thrombotic condition comprising the step of orally feeding to a patient having a thrombotic condition from about 1 to 100 mg kg of body weight per day in at least two spaced doses at least one agent having the formula:

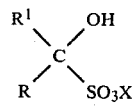

where:
R is a radical selected from the group consisting of hydrogen and hydroxymethyl,
$R^1$ is a radical selected from the group consisting of hydrogen and straight chain alkyl radicals each containing a total of 2, 3, 4, or 5 hydroxylated carbon atoms, and a residue from a polysaccharide capable of reducing Fehling's solution, and
X is selected from the group consisting of alkali metals and ammonium.

3. The method of claim 2 wherein after said feeding has started, said dose rate is adjusted to a value which is sufficient to cause a desired degree of change in at least one coagulation factor of such patients blood.

4. The method of claim 3 wherein said adjusting is periodically performed.

5. The method of claim 1 wherein said agent is sodium formaldehyde bisulfite.

6. The method of claim 2 wherein said agent is in the form of an aqueous solution.

7. A method for treating a thrombotic condition comprising the steps of injecting into a patient having a thrombotic condition at a dose rate of from about 1 to 100 mg per kg of body weight per day in at least two spaced doses at least one agent having the formula:

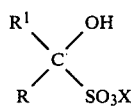

where:
R is a radical selected from the group consisting of hydrogen and hydroxymethyl,
R¹ is a radical selected from the group consisting of hydrogen and straight chain alkyl radicals each containing a total of 2, 3, 4, or 5 hydroxylated carbon atoms, and a residue from a polysaccharide capable of reducing Fehling's solution, and
X is selected from the group consisting of alkali metals and ammonium.

8. The method of claim 7 wherein after said injecting has started said dose rate is adjusted to a value which is sufficient to cause a desired degree of change in at least one coagulation factor of such patient's blood.

9. The method of claim 7 wherein said adjusting is periodically performed.

10. The method of claim 7 wherein said agent is in the form of an aqueous solution.

11. The method of claim 5 wherein said sodium formaldehyde bisulfite is orally fed in a dose form selected from the group consisting of capsules and tablets.

12. A method for preventing thrombosis of deep veins following surgery in a human patient comprising the step of treating said human patient post-operatively with an antithrombotically effective amount of at least one agent having the formula:

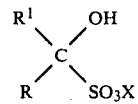

where:
R is a radical selected from the group consisting of hydrogen and hydroxymethyl,
R¹ is a radical selected from the group consisting of hydrogen and straight chain alkyl radicals each containing a total of 2, 3, 4, or 5 hydroxylated carbon atoms, and a residue from a polysaccharide capable of reducing Fehling's solution, and
X is selected from the group consisting of alkali metals and ammonium.

13. The method of claim 2 wherein said agent is orally fed to a patient at a dose rate of from about 20 to 50 mg per kg of body weight per day in at least two spaced doses.

14. The method of claim 1 wherein said thrombotic condition is demonstrated by the presence of an existing thrombus in such mammal.

15. The method of claim 1 wherein said thrombotic condition is demonstrated by the existence of an incipient thrombotic condition in such patient.

16. The method of claim 7 wherein said agent is prepared from a monosaccharide.

17. The method of claim 16 wherein said monosaccharide is glucose.

18. The method of claim 7 wherein said agent is prepared from a polysaccharide.

19. The method of claim 18 wherein said polysaccharide is lactose.

20. The method of claim 18 wherein said polysaccharide is a dextrin.

* * * * *